United States Patent [19]

Osswald et al.

[11] Patent Number: 4,766,149

[45] Date of Patent: Aug. 23, 1988

[54] USE OF N-LOW-ALKYL GLYCINES, THEIR ACID AMIDES AND OF SARCOSINE ANHYDRIDE AS TUMOR-INHIBITING ACTIVE SUBSTANCES, A REMEDY CONTAINING THE FORMER AND A PROCESS FOR ITS MANUFACTURE

[75] Inventors: Hans Osswald; Mahmoud Youssef, both of Heidelberg, Fed. Rep. of Germany

[73] Assignee: Stiftung Deutsches Krebsforschungszentrum, Heidelberg, Fed. Rep. of Germany

[21] Appl. No.: 861,753

[22] Filed: May 8, 1986

Related U.S. Application Data

[63] Continuation of Ser. No. 379,445, May 18, 1982, abandoned, which is a continuation-in-part of Ser. No. 58,187, Jul. 17, 1979, abandoned.

[30] Foreign Application Priority Data

Jul. 20, 1978 [DE] Fed. Rep. of Germany ....... 2832009

[51] Int. Cl.⁴ ............................................ A61K 31/135
[52] U.S. Cl. ...................................................... 514/553
[58] Field of Search .......................................... 514/553

[56] References Cited

PUBLICATIONS

Field et al., Cancer Research, Supplement No. 2, 1955, pp. 3-5 and 31.
The Merck Index, 9th ed, Merck & Co., Inc., Rahway, N.J., 1976 p. 359.

*Primary Examiner*—Jerome D. Goldberg
*Attorney, Agent, or Firm*—Robbins & Laramie

[57] ABSTRACT

Sarcosine and certain sarcosine derivatives, specifically N-low alkyl glycines with 1 to 4 carbon atoms in the N-alkyl part, their acid amides and sarcosine anhydride exhibit a tumor-inhibiting effect alone for themselves and mixed with one another, as well as a synergistic effect in combination with other tumor-inhibiting compounds, in particular antineoplastic alkylating compounds, intercalating substances, antimetabolites and plant substances.

10 Claims, No Drawings

USE OF N-LOW-ALKYL GLYCINES, THEIR ACID AMIDES AND OF SARCOSINE ANHYDRIDE AS TUMOR-INHIBITING ACTIVE SUBSTANCES, A REMEDY CONTAINING THE FORMER AND A PROCESS FOR ITS MANUFACTURE

RELATED APPLICATIONS

This application is a continuation of application Ser. No. 379,445, filed May 18, 1982, now abandoned, which is a continuation-in-part of application Ser. No. 58,187, filed July 17, 1979 now abandoned, the disclosure of which is incorporated herein by reference.

BACKGROUND OF THE INVENTION

There exists a great need for improving the chemotherapy of malignant tumors. To date, tumors were treated mainly by antineoplastic chemotherapeutic drugs, among them in particular the antimetabolites, alkylators and intercalating substances, as well as biosynthetic products. Since these preparations affect not only tumor cells but also other rapidly growing systems of the organism, for instance blood-forming centers, skin- and adhering structures, mucosa and germ epithelium, the therapeutic success is limited by undesirable effects.

STATEMENT OF THE INVENTION

The increase of the chemotherapeutic action without an increase of the toxic effect is therefore a desirable objective. It was found that the use of sarcosine (N-methyl glycine) and of some sarcosine derivatives, notably N-low-alkyl glycines with 1 to 4 carbon atoms in the N-alkyl portion, their acid amides and of sarcosine anhydride alone or in a mixture exhibits a favorable effect as a tumor-retarding agent in various tumors, in particular in combination with other tumor-retarding agents, whereby especially the alkyl compounds and intercalating substances are worth mentioning.

A remedy for the treatment of asthenia is known from the No. FR-A-20 80 637, which constitutes a mixture of 6 precisely defined amino acids, among which is also sarcosine. The desired effect will occur only with the use of this mixture of substances and sarcosine by itself is ineffectual.

By using sarcosine for the treatment of tumors, the therapeutic (tumor-inhibiting) effect of adriamycin or cyclophosphamide on transplantable tumors can be more than doubled without increasing toxic side effects. Because sarcosine as an amino acid exhibits an extraordinarily low toxicity, it does not have any toxic effects in the dosage to be considered for practical application.

The invention also relates to a process for the manufacture of an improved antitumor agent by combination of (a) at least one member of the group N-low-alkyl glycines with 1 to 4 carbon atoms in the N-alkyl part, amides of the former, as well as sarcosine anhydride with (b) a customary antitumor agent, especially of the type known as cytostatics. Such antitumor agents are, e.g. described in Ullmann'S Encyclopedia of Technical Chemistry, 4th edition, vol. 9, pages 705 to 714 under the designation "Cytostatics". Of special interest in this connection are antineoplastic alkylator, intercalating agents and antimetabolites.

The process involves combining (a) and (b) by bringing both components into intimate contact, preferably in a solution, generally in quantities of 2:1 to 50:1 parts by weight, especially 2:1 to 10:1 parts by weight of (a):(b). The combination obtained is insulated in a manner known per se, for example by vacuum drying, freeze drying, or by any other suitable measure, and can be produced in the usual manner in units containing an effective quantity, for instance by encapsulation or granulation, if desired together with customary fillers, excipients, and/or other suitable adjuvants. The combination product can be manufactured also in the form of injection preparations.

Frequently it is also possible to use only one of the two components as a solution in a suitable solvent and to admix the other component into this solution in powder form, and to isolate the products obtained after vigorous stirring and short reaction time. It is expedient, however, to have both of the components in form of a solution, in particular in the same solvent. If solvents are used which are unsuitable for injection preparations, they must be removed in a known manner, and only then is the combination product to be manufactured as an injection preparation. The solubilities of the reaction participants are known and can be gathered from pertinent publications. However, suitable solvents and reaction conditions can also be determined easily by a few tests. It is important to observe the directions concerning the stability of the known cytostatics, so that this reaction component is not decomposed in the reaction or isolation.

Because of the high toxicity of most cytostatics, it is usually more expedient to manufacture the preparations according to their toxicity $LD_{50}$ by combining (a) and (b) in such a way that in general 1/10 to 1/20 of the $LD_{50}$ of (b) with 1/20 to 1/100 of the $LD_{50}$ of (a) ($LD_{50}$ in mg per kg) is present for the manufacture of a standard dosage. The preferred standard dosages have a big safety margin and contain thus about 1/15 of the $LD_{50}$ of (b) combined with 1/20 to 1/40, especially 1/25 to 1/30, of the $LD_{50}$ of (a), whereby the standard dosage is based on the usual average weights of the patients to be treated who have been recorded statistically in this area and are known.

It may sometimes be preferable to encapsulate (a) and (b) in such a way or to combine them in form of a combination tablet, that one of the components (a) or (b) is present partially separated in a form ensuring delayed delivery to the body, for instance in a separate capsule which is then contained in the total capsule containing also the combination preparation. Methods of this type of encapsulation or preparation of combination tablets or dragees are well known. In this method, only one part of the reaction partner (a) and (b) is transformed prior to encapsulation or tablet forming or granulation, whereas one part of (a) or (b) is present separately, making it possible to differentiate with respect to the time of delivery to the body.

The use of sarcosine and of the sarcosine derivatives cited in combination with the aforementioned antineoplastic chemotherapeutic drugs increases actually their therapeutic effect synergistically without increase of the toxic side effects. The desired success is frequently greatest if the action of the components occurs in time intervals, whereby usually the antineoplastic agent is caused to act first, with sarcosine or the sarcosine derivative becoming effective later on, which is readily possible with the application of the combination preparation cited, one component of which is delivered delayed to the body. Especially with intercalating agents, however, the simultaneous action of both components has proven to be useful.

Of interest is also the fact that, e.g., tumors implanted intracerebrally (into the brain), which cannot be influenced by cyclophosphamide, can be cured by combining cyclophosphamide and sarcosine in over 50% of the test animals. Thus, there exists the possibility for a substantial improvement of the therapeutic possibilities in the treatment of tumors.

This characteristic of sarcosine and certain sarcosine derivatives seems to be quite specific, since, for instance, sarcosine, sarcosine anhydride (sarcosine AH), N-methyl glycine amide and N-propyl glycine amide demonstrate a tumor-retarding effect in various transplantation tumors, while, interestingly creatine, an isourea derivate of sarcosine is ineffective.

The following examples illustrate the invention. The animal tests were conducted with mice and rats, respectively. The tables 2, 3, 5, 8 and 9 include results of tests in which a compound usable pursuant to the invention and another tumor-inhibiting compound were administered at different times, in order to create in this way leuke-model tests for the application of combination drugs pursuant to the invention with delayed delivery of one component.

EXAMPLE 1

Effect of sarcosine and N-alkyl glycine amides per se, and in combination with cyclophosphamide, abbreviated thereafter by CPA and known under the trade name "endoxan", as an additional tumor-inhibiting compound (results in tables 1 to 3).

A test of sarcosine and various sarcosine derivatives in leukemia P 388 had the result that curative rates of similar extent as with cyclophosphamide, used as a positive control substance, were attained, as shown in the attached table 1. N-propanol glycine amide (series 2), which has been included as a comparison substance (just as CPA in the series 10 and 11), in table 1 proved to be less effective with respect to the curative rate (5 of 10 animals cured) and ILS (life extension of the treated series compared to the control series in percent), although it is closely related to the N-propyl-glycine amide (series 9).

In contrast, sarcosine proved its superiority to CPA employed as a positive control (series 10 and 11) with a one-time dosage of 270 mg/kg both with respect to the curative rate (11 of 15 animals cured) and the survival rate. When the sarcosine dosage of 270 mg/kg was repeated after 48 hours (series 4), the curative and survival rate increased. Sarcosine anhydride, designated here and thereafter as sarcosine AH (series 5, 6), when used in equimolar dosage like sarcosine, had with one-time administration a comparatively weaker chemotherapeutic effect (series 5). When two doses of sarcosine anhydride are administered at an interval of 48 hours, the curative and survival rate increases. In contrast, N-methyl glycine amide reaches its maximum effect already with a one-time dosage (series 7) and this effect could no longer be increased by administration of two identical dosages. N-propyl glycine amide (series 9), just as N-methyl glycine amide, had clearly a chemotherapeutic effect after administering one dosage.

The dosage for the individual preparation can be varied. Comprehensive studies conducted with sarcosine and sarcosine anhydride showed in the meantime that sarcosine was most effective with a dosage range of 150 to 370 mg/kg, whereas sarcosine anhydride showed the best chemotherapeutic effect at 200 to 320 mg/kg. Increases exceeding the range cited did no longer result in an increase of the chemotherapeutic effect. Also, the application of an equitoxic dosage of sarcosine and its derivatives should be considered, as demonstrated in the following statements. Since cyclophosphamide served as a comparison substance in the tests discussed, it seems of interest to draw a comparison between the chemotherapeutically used CPA-dosage of 30 and 60 mg/kg respectively and the lethal dosage 50 ($LD_{50}$) which is 450 mg/kg for CPA when administered subcutaneously. Taking the lowest therapeutically used dosage of CPA as a basis, a factor of 15 results, i.e. 15 times the dosage of 30 mg/kg corresponds to the $LD_{50}$ of CPA.

The $LD_{50}$ for sarcosine lies at 6500 mg/kg. The difference between the smallest dosage of sarcosine used in this test (270 mg/kg) and the $LD_{50}$ of sarcosine results in a factor of 23, i.e. the 23 times higher dosage of the therapeutically used dosage of sarcosine corresponds to the $LD_{50}$ of sarcosine. The $LD_{50}$ for sarcosine anhydride was 8300 mg/kg. In the test system used (leukemia p 388), sarcosine and its derivatives offer therefore advantages over CPA because of their lower toxicity. In a comparison test of sarcosine and sarcosine anhydride conducted on leukemia L 1210, sarcosine anhydride exhibited an even slightly better tumor-inhibitory effect than sarcosine.

As has already been mentioned, a very interesting and therefore preferable area of application for sarcosine and the derivatives cited exist in combination with other tumor-retarding agents, especially with alkylator and intercalating substances, whereby worth mentioning of the alkylators are primarily cyclophosphamide and 1,3-bis-(2-ethyl chloride)-3-(cyclohexyl)-1-nitrosourea and other 2-ethyl chloride-1-nitrosourea derivatives, and as intercalating substances especially adriamycin, dactinomycin, chlorambucil, and melphalan. Worth mentioning for the combination with metabolites are primarily etoposid (trade name "vepeside J").

Sarcosine and sarcosine derivatives with free carboxyl group or basic nitrogen still available for salt formation can be used as a customary salt, for instance as alkali- or ammonium salt, by means of which the solubility is usually improved.

Worth mentioning as an example is the combination of sarcosine with CPA in Lewis-lung carcinoma of the mouse. The Lewis-lung carcinoma constitutes one of the few transplantable tumors distinguished by forming of metastasis. The Lewis-lung carcinoma is a bronchial carcinoma of the mouse which, after implantation in the muscles of the hind thigh, will lead within a relatively short period to extensive metastasizing in the lung.

Table 2 shows that CPA was administered in a one-time increasing dosage (80, 120, 160 mg/kg) and also in three doses of 80 mg/kg weekly and 120 mg/kg weekly (series 2 to 6). With one-time dosage of 80 mg/kg CPA (series 2), the curative rate was 2 of 15 animals, the increase of life span 110%.

In a combination of 80 mg/kg CPA with 270 mg/kg of sarcosine, whereby as a model test the combination partners were administered in intervals of 6 hours (series 7), 10 of 15 animals were cured and the increase of life span amounted to 187%. A comparison of the effect of the curative rate and increase of life span in the CPA-sarcosine combination (series 7) with the chemotherapeutic effect of the doubled CPA dosage (series 5) demonstrates that the curing rate (4 of 15 animals) is distinctly lower. The calculation of the difference of the cured animals which received 80 mg/kg CPA (series 2) compared to the CPA-sarcosine combination (series 7) in the four fields-test with a preset value of $2\alpha \sim 0.5$ results in a statistically significant difference. The importance of the time interval between the effect of CPA and sarcosine becomes evident in series 8 and 9. An extension of the time interval to 8 hours leads only to a minor change of the cure- and survival rate (series 8). On the other hand, a shortening of the time interval to 3 hours (series 9) causes a distinct decrease of the cure- and survival rate. Although substantial differences exist with respect to the doubling time of the tumor and also in the generation time of the tumor cells between the Lewis-lung carcinoma and the Ehrlich carcinoma and the sarcoma 180 respectively, the time interval of 6 hours between CPA and, respectively, other alkyl compounds proves to be the optimum, whereby a general range of ca. 4 to 18 hours can be cited.

Table 3 represents the results of the combinations with cyclophosphamide and sarcosine. The treatment started after an average tumor weight of 3.5 g was reached in order to obtain tougher test conditions. The Ehrlich-carcinoma of the mouse and a treatment duration of four weeks were elected as the tumor model. With a CPA dosage of 120 mg/kg (series 2), no tumor cure is attained, but the result is a distinct retardation of tumors. When the CPA dosage is doubled to 240 mg/kg (series 3), 5 of 15 animals are cured. Sarcosine administered in monotherapy (series 4) does not show here a tumor-inhibiting effect. The combination of sarcosine with CPA (series 5) leads to a significant curative effect (10 of 15 animals cured). As CPA was used in all combinations in a dosage of 120 mg/kg, it is evident that the sarcosine/CPA combination exceeds clearly the curative effect of the doubled CPA dosage in series 3. The simultaneous administration of sarcosine and CPA (series 6) shows an increase in effect compared to the CPA monotherapy (series 2).

The CPA/sarcosine combination with a time interval of three hours (series 7) results in an increased curative effect. A significant difference compared to series 3 (CPA monotherapy) results from the combination of CPA with sarcosine with a time interval of 6 hours (series 8, 12 of 15 animals cured). The curative effect decreases again with a longer time interval (series 9, 18 hours). Conspicuous differences are shown furthermore in a comparison of the difference in body weight between the beginning and end of the test within the series treated with CPA (see last column) and the CPA/sarcosine combinations. It is clearly evident that the loss of body weight in the CPA/sarcosine combinations is less than in the CPA series.

EXAMPLE 2

Effect of adriamycin as an additional tumor-retarding compound by itself and in combination with sarcosine (results in tables 4 and 5).

Table 4 illustrates that adriamycin administered intravenously in a dosage of 2.5 mg/kg (series 2) did not have a curative effect on sarcoma 180 and failed to effect a usable inhibition of the average tumor weight. The average tumor weight was retarded by less than 50% compared to the control (series 1). The simultaneous administration of the adriamycin/sarcosine combination (series 3) had the effect that 6 of 10 animals were cured, with a significant inhibition of the tumor weight in the noncured animals.

In table 5, adriamycin was administered also against sarcoma 180 in an increased dosage (8 mg/kg intravenously) (series 2). This dosage resulted in significantly inhibiting the tumor growth compared to the control series. However, the curative effect in this series (1 of 15 animals cured) was accompanied also by toxic side effects (1 of 15 animals died). In contrast, the sarcosine/adriamycin combination with time interval led to a significant increase of the curative rate (9 of 15 animals cured) without any mortality rate by toxic side effects. A similar trend is evident in a comparison of the difference in body weight of both of the groups treated. It is conspicuous here that in all control series the difference in body weight between the beginning and the end of the test is relatively high. This is explained by the tumor cachexia occurring as a result of the progressive uninhibited growth of the tumor.

As shown by further tests, there is also the possibility of a combination with other tumor-inhibiting antineoplastic chemotherapeutics, whereby the advantage also of these combinations exists in the fact that a synergistic antineoplastic effect is obtained without increase of the toxicity, as sarcosine and its derivatives exhibit only a low toxicity. This offers the possibility of producing combination drugs for the simultaneous administration of sarcosine and/or a sarcosine derivative, especially with intercalating substances, whereby primarily the combination sarcosine/adriamycin should be mentioned.

The tests described in example 1 are compiled in the following tables 1, 2, and 3, and the tables 4 and 5 reflect the results of the tests described in example 2.

TABLE 1

| Series No. | Preparation | Single dosage mg/kg | Total dosage mg/kg | Cured | Died | ILS % (90 d) | Average time of survival |
|---|---|---|---|---|---|---|---|
| 1 | Control | — | — | — | 15/15 | — | 7–10.73–14 |
| 2 | N—propanol-glycine amide sc. | 450 | 450 | 5/15 | 10/15 | 16.03 | 10–12.7–16 |
| 3 | Sarcosine sc. | 270 | 270 | 11/15 | 4/15 | 135.47 | 10–12.5–13 |
| 4 | Sarcosine sc. | 270 | 270 | 13/15 | 2/15 | 157.22 | 10–12–14 |
| after 48 h | Sarcosine sc. | 270 | 270 | | | | |
| 5 | Sarcosine AH sc. | 260 | 260 | 6/15 | 9/15 | 85.15 | 13–13.1–14 |
| 6 | Sarcosine AH sc. | 260 | 260 | | | | |
| after 48 h | Sarcosine AH sc. | 260 | 260 | 8/15 | 7/15 | 106,89 | 13–13.28–15 |
| 7 | N—methyl glycine amide | 318 | 318 | 9/15 | 6/15 | 112.48 | 10–12–13 |
| 8 | N—methyl glycine amide sc. | 318 | 318 | 8/15 | 7/15 | 100.02 | 10–11.71–13 |
| after 48 h | N—methyl | 318 | 318 | | | | |

TABLE 1-continued glycine amide

| Series No. | Preparation | Single dosage mg/kg | Total dosage mg/kg | Cured | Died | ILS % | Average time of survival |
|---|---|---|---|---|---|---|---|
| 9 | N—propyl glycine amide sc. | 380 | 380 | 9/15 | 6/15 | 113.73 | 10–12.3–15 |
| 10 | CPA sc. | 30 | 30 | 9/15 | 6/15 | 126.15 | 14–15.66–17 |
| 11 | CPA sc. | 60 | 60 | 10/15 | 5/15 | 107.51 | 14–18.4–22 |

Strain: $D_2B_6F_1$
Tumor: P 388
Transpl. mode: ip. $10^5$ tumor cells
Transpl. date: 5-16-1978
Start of therapy: 5-17-1978
Days of treatment: Once a week
Duration of therapy: 1 week
End of test: 6-9-1978
Number of animals/series: 15

TABLE 2

| Series No. | Preparation | Single dosage mg/kg | Total dosage mg/kg | Cured | Died | ILS % | Average time of survival |
|---|---|---|---|---|---|---|---|
| 1 | Control | — | — | — | 15/15 | — | 27–27–29 |
| 2 | CPA sc. 1 × treatment | 80 | 80 | 2/15 | 13/15 | 110.9 | 37–53.0–68 |
| 3 | CPA sc. 1 × treatment | 120 | 120 | 1/15 | 14/15 | 60.5 | 36–40.7–55 |
| 4 | CPA sc. | 120 | 360 | 3/15 | 12/15 | 139.3 | 47–59.6–61 |
| 5 | CPA sc. 1 × treatment | 160 | 160 | 4/15 | 11/15 | 135.9 | 47–55.6–70 |
| 6 | CPA sc. | 80 | 240 | — | 15/15 | 92.5 | 43–56.8–60 |
| 7 after 6 h | CPA sc. Sarcosine sc. | 80 270 | 240 810 | 10/15 | 5/15 | 187.4 | 44–56.8–60 |
| 8 after 8 h | CPA sc. Sarcosine sc. | 80 270 | 240 810 | 9/15 | 6/15 | 169.7 | 36–50.1–60 |
| 9 after 3 h | CPA sc. Inosin sc. | 80 200 | 240 600 | 5/15 | 10/15 | 147.1 | 47–56.8–60 |

Strain: $D_2B_6F_1$
Tumor: Lewis lung carcinoma
Transplantation mode: Intramuscularly
Weight of tumor at the: 1.2 g - start of therapy after 5 days
Date of transplantation: March 1, 1978
Start of therapy: March 6, 1978
Days of treatment: Once a week
Duration of therapy: 1 or three weeks
End of test: April 30, 1978
Number of animals/series: 15

TABLE 3

| Series No. | Preparation | Single dosage mg/kg | Total dosage mg/kg | Cured | Died | Average weight of tumor | Average difference of body weight |
|---|---|---|---|---|---|---|---|
| 1 | Control | — | — | — | — | 16.9 | −21.3% |
| 2 | CPA | 120 | 480 | — | — | 3.3 | −15.3% |
| 3 | CPA | 240 | 960 | 5/15 | — | 2.4 | −19.3% |
| 4 | Sarcosine | 280 | 1120 | — | — | 14.7 | −21.1% |
| 5 after 4 h | Sarcosine sc. CPA sc. | 280 120 | 1120 480 | 10/15 | — | 1.4 | −7.7% |
| 6 | CPA + Sarcosine | 120 280 | 480 1120 | 2/15 | — | 3.2 | −7.1% |
| 7 after 3 h | CPA sc. Sarcosine | 120 280 | 480 1120 | 4/15 | — | 2.4 | −4.5% |
| 8 after 6 h | CPA sc. Sarcosine | 120 280 | 480 1120 | 12/15 | — | 2.5 | −2.8% |
| 9 after 18 h | CPA sc. Sarcosine sc. | 120 280 | 480 1120 | 6/15 | — | 3.1 | −7.3% |

Strain: Swiss
Tumor: Ehrlich-dpl.
Transplantation mode: Intramuscularly
Weight of tumor at start of treatment: 3.8 g
Date of transplantation: March 3, 1977
Start of therapy: March 8, 1977
Days of treatment: Once weekly
Duration of therapy: 4 weeks
End of test: April 4, 1977

TABLE 3-continued

| Series No. | Preparation | Single dosage mg/kg | Total dosage mg/kg | Cured | Died | Average weight of tumor | Average difference of body weight |
|---|---|---|---|---|---|---|---|
| | Number of animals/series: | | 15 mice | | | | |

TABLE 4

| Series No. | Preparation | Single dosage mg/kg | Total dosage mg/kg | Cured | Died | Average weight of tumor | Average difference in body weight |
|---|---|---|---|---|---|---|---|
| 1 | Control | — | — | — | — | 14.7 | −26.3% |
| 2 | Adriamycin intravenously | 2.5 | 10 | — | — | 8.9 | −17.0% |
| 3 | Adriamycin + Sarcosine intravenously | 2.5 200 | 10 800 | 6/15 | — | 2.9 | −10.1% |

| | |
|---|---|
| Strain: | Swiss |
| Tumor: | Sarcoma 180 |
| Mode of transplantation | Intramuscularly |
| Weight of tumor at start of treatment | 1.2 g |
| Date of transplantation | Jan. 21, 1977 |
| Start of therapy | Jan. 24, 1977 |
| Days of treatment: | Once a week |
| Duration of therapy: | 4 weeks |
| End of test: | Feb. 26, 1977 |
| Number of animals/series | 15 mice |

TABLE 5

| Series No. | Preparation | Single dosage mg/kg | Total dosage mg/kg | Cured | Died | Average weight of tumor | Average difference in body weight |
|---|---|---|---|---|---|---|---|
| 1 | Control | — | — | — | — | 15.1 | −14.3% |
| 2 | Adriamycin intravenously | 8 | 24 | 1/15 | 1/15 | 5.4 | −9.9% |
| 3 | Sarcosine intravenously | 180 | 540 | 9/15 | — | 5.0 | −3.5% |
| after 2 h | Adriamycin intravenously | 8 | 24 | | | | |

| | |
|---|---|
| Strain: | Swiss |
| Tumor: | Sarcoma 180 |
| Mode of transplantation | Intramuscularly |
| Weight of tumor at start of treatment | 0.7 g |
| Date of transplantation: | Nov. 29, 1976 |
| Start of therapy: | Dec. 1, 1976 |
| Days of treatment: | Once a week |
| Duration of therapy: | 3 weeks |
| End of test: | Dec. 28, 1976 |
| Number of animals/series: | 15 mice |

EXAMPLE 3

Comparison of the chemotherapeutic effect of sarcosine with sarcosine anhydride (sarcosine AH), as well as CPA on the intramuscularly implanted DS-carcinosarcoma (table 6).

The therapy was started when the tumor growth had progressed far (tumor size 4.5 to 5.0 grams). The resistance of the tumor against cyclophosphamide can be seen from series 2. The difference between the weight of the tumor in the control series (series 1) and the series treated with CPA (28.6 g/20.1 g) is very minor.

On the other hand, in a one-time subcutaneous administration of 180 mg/kg per week, sarcosine had a curative effect in 8 of 10 rats (series 3). Interestingly, a subcutaneous administration of 180 mg/kg of sarcosine three times a week did not effect an improvement of the curative or tumor-inhibiting effect. Sarcosine AH (sarcosine anhydride) has a curative effect in 10 of 10 rats already with a one-time subcutaneous administration of 290 mg/kg (series 5), and the same result is attained with three times subcutaneous administration of 290 mg/kg sarcosine AH (series 6). It appears that sarcosine and sarcosine anhydride intervene in precursors of the purine synthesis, whereby, depending on the type of tumor involved, differences result in the degree of effectiveness of sarcosine and sarcosine anhydride when both preparations are used in equimolar dosage. The great sensibility of the DS-carcinosarcoma against sarcosine and sarcosine anhydride opens the possibility of clarifying the biochemical effect mechanism and of bringing the question of the missing toxicity also with higher dosages closer to a solution with respect to normal, proliferating systems (e.g. blood-forming centers in the bone marrow).

The results are compiled in the following table 6.

TABLE 6

| Series No. | Preparation | Single dosage mg/kg | Total dosage mg/kg | Cured | Died | Average weight of tumor ± |
|---|---|---|---|---|---|---|
| 1 | Control | — | — | — | — | 28.6 ± 1.7 |
| 2 | CPA intrav. | 60 | 120 | — | — | 20.1 ± 1.0 |
| 3 | Sarcosine sc. | 180 | 360 | 8/10 | — | 19.6 ± 1.5 |
| 4 | Sarcosine sc. 3 × weekly Mo. Wed. Fri. | 180 | 720 | 8/10 | — | 20.7 ± 1.3 |
| 5 | Sarcosine AH sc. | 290 | 580 | 10/10 | — | — |
| 6 | Sarcosine AH sc. 3 × weekly Mo. Wed. Fri. | 290 | 1160 | 10/10 | — | — |

Strain: SD-rats
Tumor: DS-carcinosarcoma
Mode of transplantation: Intramuscularly
Weight of tumor at beginning of treatment: 4.5 to 5.0 g
Date of transplantation: March 12, 1979
Start of therapy: March 21, 1979
Duration of therapy: 2 weeks
End of test: April 2, 1979
Number of animals/series: 10

EXAMPLE 4

Comparison of sarcosine anhydride with CPA in the DS-carcinosarcoma of the rat (table 7).

It is known from numerous data in the literature (for instance Brock, N.: "Experimental Basis of Cancer Chemotherapy", Chemotherapy 7, 19 to 50 (1976) that the DS-carcinosarcoma can be influenced only little by CPA. In the present test, CPA was tested in comparison with sarcosine anhydride. This should be qualified by mentioning that CPA is still tolerated in a weekly dosage of 80 mg/kg, while sarcosine anhydride is well tolerated in a daily subcutaneous administration of 2×200 mg/kg. It is shown that CPA effects curing of a tumor in 2 of 10 animals with a dosage of 60 mg/kg, whereas the remaining animals experience practically no retardation of the tumor growth, as is evident from the comparison of the average tumor weights in the control- and CPA series (series 1, 2). In a dosage of 290 mg/kg sc (3×weekly), sarcosine anhydride leads in 8 of 10 animals to a complete regression of the tumor. The inhibition of the tumor in the two noncured animals appears insignificant.

The results are summarized in the following table 7.

TABLE 7

| Series No. | Preparation | Single dosage mg/kg | Total dosage mg/kg | Cured | Died | Average weight of tumor ± |
|---|---|---|---|---|---|---|
| 1 | Control | — | — | — | — | 16.2 ± 1.48 |
| 2 | CPA sc. once a week | 60 | 180 | 2/10 | — | 15.3 ± 2.1 |
| 3 | Sarcosine AH sc. 3 × a week | 290 | 2320 | 8/10 | — | 12.4 ± 1.2 |

Strain: Sprague-Dawley
Tumor: DS-carcinosarcoma
Mode of transplantation: Intramuscularly
Weight of tumor at start of treatment: Average 1.5 g
Date of transpl.: Feb. 15, 1979
Start of therapy: Feb. 21, 1979
Days of treatment: Mo., Wed., Fri.
Duration of therapy: 3 weeks
End of test: March 9, 1979
Number of animals/series: 10

EXAMPLE 5

Comparison of the chemotherapeutical effect of various dosages of VM 26 and sarcosine anhydride and of their combination on the diploid, intracerebrally implanted Ehrlich-Ascites tumor (results in table 8).

VM 26, an epipodophyllotoxin derivative which is a 4'-dimethyl epipodophyllotoxin, is used in acute myeloic leukemia, neurogenic tumors, and malignant lymphoma, whereby the results gathered to date appear interesting especially in neurogenic tumors.

The tests show the following:

VM 26, the clinical area of application of which comprises brain tumors and Hodgkin's disease, has, depending on the dosage administered in the intracerebrally implanted Ehrlich-Ascites tumor, a chemotherapeutic effect (series 2 to 4) which, however, has a pronounced curative effect (10 of 15 mice cured) only by administration of 18 mg/kg intravenously weekly. The combination of VM 26 (6 mg/kg) and sarcosine anhydride (290 mg/kg) surpasses, with simultaneous administration, the curative effect of the three times higher monotherapy with VM 26 (series 5). All the animals are cured. In contrast, a decreasing curative effectiveness of the combination VM 26 and sarcosine anhydride results when the time interval between the combination partners is 3 or 6 hours (series 6, 7). Sarcosine anhydride does not have any effect on the survival rate when administered once, as used in the combination with VM 26 (series 8). However, the dosage of sarcosine anhydride administered on five consecutive days leads to a cure in 13 to 15 mice (series 9), while a single administration of 1150 mg/kg of sarcosine anhydride leads to a cure in 8 of 15 mice (series 10).

Sarcosine anhydride is tolerated in daily subcutaneous administration of 2×2500 mg/kg over a period of 14 days without loss of weight, whereas VM 26 can be given only once a week (for a total of 14 days) intravenously in a dosage of 18 mg/kg without causing severe toxic injury. Aside from the combination effect of sarcosine anhydride with VM 26, it appears of interest that a distinct curative effect can be attained by sole use of a higher dosage or daily administration of sarcosine anhydride.

anhydride do not exhibit any significant tumor-inhibiting effect. VM 26 administered in monotherapy causes

TABLE 8

| Series No. | Preparation | Single dosage mg/kg | Total dosage mg/kg | Cured | Died | Average time of survival |
|---|---|---|---|---|---|---|
| 1 | Control | — | — | 0/15 | 15/15 | 6–6, 5–8 |
| 2 | VM 26 intrav. | 6 | 12 | 3/15 | 12/15 | 6–9, 3–13 |
| 3 | VM 26 intrav. | 12 | 24 | 4/15 | 11/15 | 7–9, 7–13 |
| 4 | VM 26 intrav. | 18 | 36 | 10/15 | 5/15 | 7–11, 8–13 |
| 5 | VM 26 intrav. + Sarcosine AH sc. | 6 290 | 12 580 | 15/15 | 0/15 | |
| 6 | VM 26 intrav. 3 h later Sarcosine AH sc | 6 290 | 12 580 | 13/15 | 2/15 | 6–7, 5–9 |
| 7 | VM 26 intrav. 6 h later Sarcosine AH sc. | 6 290 | 12 580 | 9/15 | 6/15 | 6–10, 1–13 |
| 8 | Sarcosine AH sc. | 290 | 580 | 0/15 | 15/15 | 6–7, 6–9 |
| 9 | Sarcosine AH sc. | 5 × 290 | 2900 | 13/15 | 2/15 | 10–11, 5–13 |
| 10 | Sarcosine AH sc. | 1150 | 2300 | 8/15 | 7/15 | 6–11, 7–14 |

| | |
|---|---|
| Strain: | Swiss mouse |
| Tumor: | Ehrlich-carcinoma diploid |
| Mode of transplantation: | Intracerebrally |
| Date of transpl.: | March 6, 1979 |
| Start of therapy: | March 7, 1979 |
| Days of treatment: | Once a week |
| Duration of therapy: | 2 weeks |
| End of test: | March 13, 1979 |
| Number of animals/series | 15 |

EXAMPLE 6

Comparison of the combinations between VM 26 with sarcosine and, respectively, sarcosine anhydride (sarcosine AH) in the intramuscularly implanted diploid Ehrlich-Ascites tumor (table 9).

In this comparative test, in which sarcosine and sarcosine anhydride were used in equimolar dosage, it was shown that, contrary to the findings made on the intracerebrally implanted Ehrlich-Ascites tumor, the optimal effect occurs with a time interval of the combination partners (VM 26 with sarcosine or sarcosine anhydride) of 6 hours. Administered once a week in the same dosage as in the combination, sarcosine and sarcosine anhydride do not exhibit any significant tumor-inhibiting effect. VM 26 administered in monotherapy causes an increasing tumor inhibition with rising dosage in the dosage range used (series 2 to 4). The combination of VM 26 and sarcosine proves clearly superior both in regard to tumor inhibition and the curing rate of the VM 26 monotherapy (series 5 to 7), whereby an increase in the curative rate is noticeable also in the combination with increasing VM 26 dosage. Similar results can be attained with the combination of VM 26 and sarcosine anhydride, whereby, however, the curative rate in the lower and medium dosage range shows a greater increase than with the highest VM 26 dosage (series 8 to 10).

The results are summarized in the following table 9.

TABLE 9

| Series No. | Preparation | Single dosage mg/kg | Total dosage mg/kg | Cured | Died | Average weight of tumor | Average difference in body weight |
|---|---|---|---|---|---|---|---|
| 1 | Control | — | — | — | — | 13.9 ± 3.2 | −12.4 |
| 2 | VM 26 intrav. | 5 | 15 | 0/15 | 0/15 | 5.8 ± 1.9 | −4.3 |
| 3 | VM 26 intrav. | 10 | 30 | 0/15 | 0/15 | 3.1 ± 1.6 | −2.3 |
| 4 | VM 26 intrav. | 15 | 45 | 1/15 | 0/15 | 2.6 ± 1.5 | −3.7 |
| 5 | VM 26 intrav. after 6 h Sarcosine sc. | 5 178 | 15 534 | 0/15 | 0/15 | 1.8 ± 0.9 | −0.2 |
| 6 | VM 26 intrav. after 6 h Sarcosine sc. | 10 178 | 30 534 | 5/15 | 0/15 | 0.9 ± 0.5 | −3.5 |
| 7 | VM 26 intrav. after 6 h Sarcosine sc. | 15 178 | 45 534 | 13/15 | 0/15 | 0.3 ± 0.1 | −4.2 |
| 8 | VM 26 intrav. after 6 h Sacrosine AH sc. | 5 284 | 15 852 | 3/15 | 0/15 | 1.0 ± 0.4 | −1.2 |
| 9 | VM 26 intrav. after 6 h Sarcosine AH sc. | 10 284 | 30 852 | 8/15 | 0/15 | 0.5 ± 0.3 | −2.3 |
| 10 | VM 26 intrav. after 6 h | 15 | 45 | 10/15 | 0/15 | 0.6 ± 0.3 | −4.7 |

TABLE 9-continued

| Series No. | Preparation | Single dosage mg/kg | Total dosage mg/kg | Cured | Died | Average weight of tumor | Average difference in body weight |
|---|---|---|---|---|---|---|---|
| | Sarcosine AH sc. | 284 | 852 | | | | |

| | |
|---|---|
| Strain: | Swiss mouse |
| Tumor: | Ehrlich carcinoma diploid |
| Mode of transpl.: | Intramuscularly |
| Weight of tumor at start of treatment: | Average 1.5 g |
| Date of transpl.: | March 9, 1979 |
| Start of therapy: | March 12, 1979 |
| Days of treatment: | Once a week |
| Duration of therapy: | 3 weeks |
| Number of animals/series: | 15 mice |

EXAMPLE 7

Comparison of the effect of cisplatinum with sarcosine alone and in combination (results in table 10).

Cisplatinum (cis-dichlorodiamine platinum, abbreviated (CPDD) possesses special importance because of its attainment of long-term remissions (in part up to five years after termination of therapy) in testicle tumors, bone sarcoma, and prostate carcinoma.

In the diploid Ehrlich-carcinoma, which was implanted intramuscularly in female Swiss mice, the treatment with cisplatinum in various dosages and cisplatinum/sarcosine combinations was performed four days after the tumor transplant with an average tumor weight of 2.5 g. We used as a positive control 120 mg/kg of CPA subcutaneously which was administered at intervals of 14 days just as the various dosages of cisplatinum administered intravenously, as well as their combinations with sarcosine. The results in the table show that CPA (series 2) effects a distinct inhibition of the tumor. Cisplatinum (series 3 to 5) in a dosage of 8 mg/kg achieves a significant tumor inhibition and a complete remission of the tumor. The simultaneous combination of cisplatinum and sarcosine (series 6 to 8) proves to be superior to the monotherapy with cisplatinum. Depending on the dosage of cisplatinum used, there is a distinct increase in the tumor inhibition and curative rate. Even the dosage of 4 mg/kg cisplatinum attains, when combined with sarcosine (series 6), a inhibition of the tumor growth by more than 50%, effecting finally with the use of 8 mg/kg cisplatinum with sarcosine (series 8) a cure in 10 of 15 animals, and in the noncured animals a more intensive inhibition of the tumor than cisplatinum used alone in the same dosage (series 5). When administered alone in intervals of 14 days, sarcosine has no chemotherapeutical effect (series 9). To be effective, substantially higher dosages would be necessary within a shorter period of time.

TABLE 10

| Series No. | Preparation | Single dosage mg/kg | Total dosage mg/kg | Cured | Died | Average weight of tumor | Average difference in body weight |
|---|---|---|---|---|---|---|---|
| 1 | Control | — | — | — | — | 14.3 ± 3.6 | −23.2% |
| 2 | CPA sc. | 120 | 360 | — | — | 4.7 ± 2.3 | −4.4% |
| 3 | CPDD intrav. | 4 | 12 | — | — | 11.1 ± 4.1 | −11.6% |
| 4 | CPDD intrav. | 6 | 18 | — | — | 7.8 ± 3.4 | −9.1% |
| 5 | CPDD intrav. | 8 | 24 | 1/15 | — | 4.3 ± 3.5 | −8.8% |
| 6 | CPDD + intrav. Sarcosine | 4 178 | 12 534 | — | — | 6.8 ± 4.5 | −3.8% |
| 7 | CPDD + intrav. Sarcosine | 6 178 | 18 534 | 2/15 | — | 4.5 ± 3.2 | −3.2% |
| 8 | CPDD + intrav. Sarcosine | 8 178 | 24 534 | 10/15 | — | 2.4 ± 2.1 | −4.2% |
| 9 | Sarcosine | 178 | 534 | — | — | 11.2 ± 3.3 | −12.1% |

| | |
|---|---|
| Strain: | Swiss |
| Tumor: | Ehrlich-carcinoma |
| Mode of transplantation | Intramuscularly |
| Weight of tumor at start of treatment: | 2.5 g |
| Date of transplantation: | Jan. 12, 1979 |
| Start of therapy: | Jan. 16, 1979 |
| Days of treatment: | 1st, 3rd and 5th week |
| Duration of therapy: | 6 weeks |
| End of test: | Feb. 19, 1979 |
| Number of animals/series: | 15 mice |

PRODUCTION EXAMPLE 1

A saturated aqueous sarcosine solution containing 28 g sarcosine is added at room temperature under vigorous stirring to a solution of 12 g CPA in 500 ml ethanol.

The reaction mass is vigorously stirred further and then freeze-dried after 10 to 15 minutes.

The residue is subsequently pressed, coated, capsuled or manufactured to an injection solution in a known manner, whereby a single dosage contains the quantity of 50 mg CPA-constituent as customary for CPA, combined with 117 mg sarcosine.

PRODUCTION EXAMPLE 2

In the same way as in the production example 1, a concentrated aqueous solution containing 18 g of sarcosine was caused to react with 8 g of adriamycin dissolved in 500 ml ethanol. The addition-product was isolated by freeze-drying. A standard dosage contains the adriamycin/sarcosine complex in a proportion of 50 mg adriamycin to 1125 mg sarcosine.

PRODUCTION EXAMPLE 3

29 g sarcosine anhydride in 250 ml water were put into a 20% ethanol solution containing 6 g VM 26. After several minutes of vigorous stirring and letting it stand, the obtained solution was freeze-dried and manufactured in a known manner to an injection preparation containing 30 mg of the VM constituent and 1450 mg of the sarcosine anhydride constituent.

PRODUCTION EXAMPLE 4

8 g cisplatinum were introduced as a 1.5% aqueous solution containing at the same time 0.9% of NaCl under vigorous stirring into an aqueous solution of 178 g sarcosine in 500 ml water. After additional vigorous stirring for 5 to 10 minutes, the reaction mixture was freeze-dried and manufactured in a known manner to an injection preparation which contained 80 mg CPDD per standard dosage.

The carrier vehicles used were as follows: the known pure antineoplastic chemotherapeutics were dissolved in a 7% glucose solution with the only exception that Cisplatin (CPDD) was dissolved in physiological saline solution (0.9% NaCl solution).

The concentrations of the solutions used for administering can be deduced relatively from the dosages used, e.g. to administer 100 mg/kg a 1% solution and to administer 10 mg/kg a 0.1% solution is utilized. When combining 100 mg/kg of one substance with 10 mg/kg of another substance the total concentration of said solution is 1.1%. In view of the fact that the single doses are given in the tables, the percentual compositions can be easily calculated.

In the following examples 8 to 24 the abbreviations used are as follows:

| | |
|---|---|
| Saran = | sarcosine anhydride |
| i.p. = | intraperitoneally |
| i.m. = | intramuscularly |
| i.c. = | intracerebrally |
| s.c. = | subcutaneously |
| i.v. = | intravenously |
| CPA = | Cyclophosphamid = "Endoxan" |
| CPDD = | cis-platinum-diamino-dichloride |
| VM 26 = | Teniposide = 4'demethyl-epidodophyllotoxine-thenylidene-glucoside = VM 26-Bristol" |
| VP = | Etoposide = semisynthetic epipodophyllotoxine-derivative = "Vepeside J" |
| MTX = | 4-amino- $^{10}$N—methylpteroyl-glutamic acid = "Methotrexate" |
| Thioph. = | thiophosphoric acid-N,N',N"—tris-(ethylene-imide) = "Thio Tepa" |
| Folic acid = | 5-formyl-5,6-7,8-tetrahydropteroyl-glutamic acid = "Leucovorine" |
| ILS = | Increase of life span |
| MST = | Median survival time |

As a carrier for the antineoplastic substances tested a 7% glucose solution was used with the only exception that CPDD was dissolved in a physiological saline solution.

EXAMPLE 8

The test condition used and the results obtained are given in Table 11.

The series 2/6/9/12, 3/7/10/13 and 4/8/11/14 show the significant synergistic curative effect of the combination sarcosine-CPA.

TABLE 11

| Series No | Preparation | Single dosage mg/kg | Total dosage mg/kg | Cured | Died | ILS % | MST days |
|---|---|---|---|---|---|---|---|
| 1 | Control Glucose sc | 1000 | 2000 | — | 15/15 | — | 25–32, 4–33 |
| 2 | CPA sc. | 68,1 | 136,2 | 1/15 | 14/15 | 24 | 27–34, 7–56 |
| 3 | CPA sc. | 82,5 | 165 | 1/15 | 14/15 | 46 | 43–45, 5–54 |
| 4 | CPA sc. | 100 | 200 | 2/15 | 13/15 | 35 | 21–41, 3–54 |
| 5 | CPA sc. | 121 | 242 | 8/15 | 7/15 | 54 | 22–37–57 |
| 6 | CPA + sc. Sarcosine | 68,1 267 | 136 534 | 2/15 | 13/15 | 45 | 35–48, 5–55 |
| 7. | CPA + sc. Sarcosine | 82.5 267 | 165 534 | 7/15 | 8/15 | 49 | 28–38, 1–57 |
| 8 | CPA + sc. Sarcosine | 100 267 | 200 534 | 12/15 | 3/15 | 74 | 42–42–42 |
| 9 | CPA + sc Sarcosine | 68,1 178 | 136,2 356 | 9/15 | 6/15 | 169 | 45–47–57 |
| 10 | CPA + sc Sarcosine | 82,5 178 | 165 356 | 5/15 | 10/15 | 69 | 42–44, 4–49 |
| 11 | CPA + sc Sarcosine | 100 178 | 200 356 | 8/15 | 7/15 | 62 | 43–44, 1–49 |
| 12 | CPA + sc Sarcosine | 68,1 89 | 136 178 | 8/15 | 7/15 | 71 | 45–49, 8–54 |
| 13 | CPA + sc. Sarcosine | 82,5 89 | 165 178 | 9/15 | 6/15 | 72 | 46–49, 6–57 |
| 14 | CPA + sc. Sarcosine | 100 89 | 200 178 | 7/15 | 8/15 | 58 | 43–43, 3–46 |

| | | | |
|---|---|---|---|
| Strain: | D$_2$B$_6$F$_1$ | Days of treatment: | Once a week |
| Tumor: | Lewis-Lung-Carcinoma | Duration of therapy: | 2 weeks |
| Mode of transplantation | Intramuscularly: | End of test: | April 12, 1980 |
| Date of transplantation: | February 8, 1980 | Number of animals/series: | 15 mice |
| Start of therapy: | February 12, 1980 | | |

EXAMPLE 9

The test conditions used and the results obtained are given in Table 12. The series 2/4/6 and 3/5/7 show the synergistic curative effect of sarcosine anhydride, whereas the same is proven for sarcosine by the series 2/8/10 and 3/9/11.

TABLE 12

| Series No. | Preparation | Single dosage mg/kg | Total dosage mg/kg | Cured | Avarage weight of tumor (g) |
|---|---|---|---|---|---|
| 1 | Control | — | — | — | 29,9 ± 4,6 |
| 2 | CPA iv. | 4 | 12 | 2/10 | 12,1 ± 7,4 |
| 3 | CPA iv. | 8 | 24 | 6/10 | 3,5 ± 1,8 |
| 4 | CPA + Saran iv. | 4 71 | 12 213 | 6/10 | 10,3 ± 3,3 |
| 5 | CPA + Saran iv. | 8 71 | 24 213 | 9/10 | 5,2 |
| 6 | CPA + Saran iv. | 4 142 | 12 426 | | |
| 7 | CPA + Saran iv. | 8 142 | 24 426 | 8/10 | 16,1 ± 4,8 |
| 8 | CPA + Sarcosine iv. | 4 89 | 12 267 | 9/10 | 10,2 |
| 9 | CPA + Sarcosine iv. | 8 89 | 24 267 | 5/10 | 10,2 ± 3,5 |
| 10 | CPA + Sarcosine iv. | 4 178 | 12 534 | 5/10 | 11,5 ± 4,3 |
| 11 | CPA + Sarcosine iv. | 8 178 | 24 534 | 8/10 | 10,7 ± 4,5 |
| 12 | Saran iv. | 71 | 213 | — | 19,4 ± 8,2 |
| 13 | Saran iv. | 142 | 426 | — | 23,7 ± 6,8 |
| 14 | Sarcosine iv. | 89 | 267 | — | 23,8 ± 5,5 |
| 15 | Sarcosine iv. | 178 | 534 | — | 23,1 ± 10,1 |

Strain: SD-rats
Tumor: Yoshida Tumor
Mode of transplantation: i.m.
Weight of tumor at start of treatment: 4,5 g
Date of transplantation: February 21, 1980
Start of therapy: February 28, 1980
Days of treatment: Once a week
Duration of therapy: 3 weeks TABLE 12-continued

| End of test: | March 17, 1980 |
|---|---|
| Number of animals/series: | 10 |

EXAMPLE 10

The test conditions used and the results obtained are given in Table 13.

The series 2/4 and 3/5 show the curative synergistic effect of sarcosine-CPDD against i.m. implanted Ehrlich-carcinoma. The fact that the onset of therapy starts at an average tumor weight of 2,5 g explains the finding that cyclophosphamide seems to have a relatively slight effect at a dose of 120 mg/kg. A comparison of the monotherapy of CPDD and the therapy with a combination of CPDD and sarcosine elucidates a marked superiority of the combination. The monotherapy with sarcosine results in a slight reduction of the average tumor weight.

TABLE 13

| Series No. | Preparation | Single dosage mg/kg | Total dosage mg/kg | Cured | Died | Average weight of tumor (g) | Average difference in body weight |
|---|---|---|---|---|---|---|---|
| 1 | Control | — | — | — | — | 14,3 ± 3,6 | −23,2% |
| 2 | CPDD iv. | 6 | 18 | — | — | 7,8 ± 3,4 | −9,1% |
| 3 | CPDD iv. | 8 | 24 | 1/15 | — | 4,3 ± 3,5 | −8,8% |
| 4 | CPDD + Sarcosine iv. | 6 178 | 18 534 | 2/15 | — | 4,5 ± 3,2 | −3,2% |
| 5 | CPDD + Sarcosine iv. | 8 178 | 24 534 | 10/15 | — | 2,4 ± 2,1 | −4,2% |
| 6 | Sarcosine iv. | 178 | 534 | — | — | 11,2 ± 3,3 | −12,1% |

Strain: Swiss
Tumor: Ehrlich-Ca.diploid
Mode of transplantation: i.m.
Body weight at start of transplantaion: 33 g (average)
Weight of tumor at start of treatment: 2.5 g (average)
Date of transplantation: January 12, 1979
Start of therapy: January 16, 1979
Days of treatment: Once a week
Duration of therapy: 3 weeks
End of test: February 19, 1979
Number of animals/series: 15 mice

EXAMPLE 11

The test conditions used and the results obtained are given in Table 14. The series 2/3 show the synergistic curative effect of sarcosine anhydride-CPDD.

TABLE 14

| Series No. | Preparation | Single dosage mg/kg | Total dosage mg/kg | Cured | Died | ILS % | MTS days |
|---|---|---|---|---|---|---|---|
| 1 | Control | — | — | — | 15/15 | — | 6–7, 7–9 |
| 2 | Cis-platin iv. | 6 | 12 | 1/15 | 14/15 | 68 | 7–11, 7–20 |
| 3 | Cis-platin + Saran iv. | 6 71 | 12 142 | 3/15 | 12/15 | 160 | 11–16, 6–27 |
| 4 | Saran iv. | 71 | 142 | — | 15/15 | 3 | 6–8, 2–11 |

Strain: Swiss
Tumor: Ehrlich-Ca.diploid
Mode of transplantation: i.c.
Body weight at start of transplantation: 30 g (average)
Date of transplantation: July 10, 1979
Start of therapy: July 11, 1979
Days of treatment: 1 + 5 times a week
Duration of therapy: 2 weeks
End of test: August 9, 1979
Number of animals/series: 15 mice

EXAMPLE 12

The test conditions used and the results obtained are given in Table 15.

The series 2/4 show the synergistic activity of sarcosine/CPDD against i.c. implanted Yoshida Sarcoma and series 8 and 10 show the curative effect of sarcosine anhydride when used in monotherapy.

TABLE 15

| Series No. | Preparation | Single dosage mg/kg | Total dosage mg/kg | Cured | Died | ILS % | MST days |
|---|---|---|---|---|---|---|---|

TABLE 15-continued

| | | | | | | | |
|---|---|---|---|---|---|---|---|
| 1 | Control | — | — | — | 10/10 | — | 7-8, 2-9 |
| 2 | CPDD iv. | 4 | 8 | — | 10/10 | 80 | 12-14, 7-20 |
| 3 | CPDD iv. + Sarcosine | 4 89 | 8 178 | — | 10/10 | 105 | 14-16, 8-19 |
| 4 | CPDD + Sarcosine iv. | 4 178 | 8 356 | 4/10 | 6/10 | 304 | 9-15, 1-18 |
| 5 | Sarcosine iv. | 178 | 356 | — | 10/10 | 14 | 7-9, 3-10 |
| 6 | Sarcosine iv. 3×(2 h) | 178 | 1068 | — | 10/10 | 16 | 9-9, 5-10 |
| 7 | Saran iv. 3×(2 h) | 142 | 852 | — | 10/10 | 22 | 9-10-11 |
| 8 | Saran iv. 3×(3 h) | 284 | 1704 | 2/10 | 8/10 | 127 | 7-8, 2-10 |
| 9 | Saran sc. 3×(2 h) | 142 | 852 | — | 10/10 | 13 | 7-9, 2-11 |
| 10 | Saran sc. 3×(2 h) | 284 | 1704 | 2/10 | 8/10 | 166 | 7-12, 2-17 |

| | |
|---|---|
| Strain: | SD-rats |
| Tumor: | Yoshida Sarcoma |
| Mode of transplantation: | i.c. |
| Body weight at start of transplantation: | 85 g (average) |
| Date of transplantation: | November 24, 1980 |
| Start of therapy: | November 25, 1980 |
| Days of treatment: | 1 + 3 times a week |
| Duration of therapy: | 2 weeks |
| End of test: | December 4, 1980 |
| Number of animals/series: | 10 |

EXAMPLE 13

The test conditions used and the results obtained are given in Table 16.

The series 2/5, 3/6 and 4/7 show the significant synergistic curative effect of sarcosine-VM 26.

TABLE 16

| Series No. | Preparation | Single dosage mg/kg | Total dosage mg/kg | Cured | Died | ILS % | MST days |
|---|---|---|---|---|---|---|---|
| 1 | Control | — | — | — | 15/15 | — | 7-7, 6-8 |
| 2 | VM 26 iv. | 3 | 6 | — | 15/15 | 43 | 8-10, 9-14 |
| 3 | VM 26 iv. | 6 | 12 | — | 15/15 | 28 | 8-8, 9-15 |
| 4 | VM 26 iv. | 12 | 24 | 3/15 | 12/15 | 142 | 7-12, 7-18 |
| 5 | VM 26 + Sarcosine iv. | 3 267 | 6 534 | 8/15 | 7/15 | 182 | 7-11, 5-16 |
| 6 | VM 26 + Sarcosine iv. | 6 267 | 12 534 | 7/15 | 8/15 | 165 | 7-11, 5-16 |
| 7 | VM 26 + Sarcosine iv. | 12 267 | 24 534 | 8/15 | 7/15 | 179 | 7-11, 4-18 |
| 8 | Sarcosine iv. | 267 | 534 | — | 15/15 | 29 | 9-9, 8-12 |

| | |
|---|---|
| Strain: | Swiss |
| Tumor: | Ehrlich Ca.-diploid |
| Mode of transplantation: | i.c. |
| Body weight at start of transplantation: | 33 g (average) |
| Date of transplantation | March 24, 1980 |
| Start of therapy: | March 25, 1980 |
| Days of treatment: | 1 + 5 times a week |
| Duration of therapy: | 2 weeks |
| End of test: | April 26, 1980 |
| Number of animals/series: | 15 mice |

EXAMPLE 14

The test conditions used and the results obtained are given in Table 17.

The results show that sarcosine anhydride is as active as VM 26 when tested against i.c. implanted Yoshida Sarcoma but its use does not lead to any deterioration of tissues like blood forming centres.

TABLE 17

| Series No. | Preparation | Single dosage mg/kg | Total dosage mg/kg | Cured | Died | ILS % | MST days |
|---|---|---|---|---|---|---|---|
| 1 | Control | — | — | — | 8/8 | — | 6-8-11 |
| 2 | VM 26 iv. | 4,6 | 9,2 | 1/8 | 7/8 | 92 | 9-13, 2-25 |
| 3 | VM 26 iv. | 6,8 | 13,6 | 2/8 | 6/8 | 108 | 6-12, 1-11 |
| 4 | Saran sc. 3×(3 h) | 284 | 1704 | 1/8 | 7/8 | 100 | 6-14, 0-27 |
| 5 | Saran sc. 3×(2 h) | 284 | 1704 | 3/8 | 5/8 | 97 | 6-7, 2-8 |

| | |
|---|---|
| Strain: | SD-rats |
| Tumor: | Yoshida Sarcoma |
| Mode of transplantation: | i.c. |
| Body weight at start of transplantation: | 80 g (average) |
| Date of transplantation: | January 21, 1981 |
| Start of therapy: | January 22, 1981 |
| Days of treatment: | Once a week |
| Duration of therapy: | 2 weeks |
| End of test: | February 21, 1981 |

TABLE 17-continued

Number of animals/series: 8

EXAMPLE 15

The test conditions used and the results obtained are given in Table 18.

The series 2/4 and 3/5 show the synergistic curative effect of sarcosine anhydride-VP 16.

EXAMPLE 16

The test conditions used and the results obtained are given in Table 19.

The series 3/7 and 4/8 show the synergistic effect of sarcosine anhydride-adriamycine.

TABLE 18

| Series No. | Preparation | Single dosage mg/kg | Total dosage mg/kg | Cured | Died | ILS % | MST days |
|---|---|---|---|---|---|---|---|
| 1 | Control | | | | | | |
| | 3×Glucose (2,5 h) orally after 24 h | 600 | 3600 | | | | |
| | 3×Glucose (2,5 h) orally after 24 h | 600 | 3600 | — | 10/10 | — | 8-9, 0-10 |
| | 3×Glucose (2,5 h) orally | 600 | 3600 | | | | |
| 2 | VP 16 3×(2,5 h) orally after 24 h | 4 | 24 | | | | |
| | VP 16 3×(2,5 h) orally after 24 h | 4 | 24 | — | 10/10 | 30 | 10-11, 7-13 |
| | VP 16 3×(2,5 h) orally | 4 | 24 | | | | |
| 3 | VP 16 3×(2,5 h) orally after 24 h | 6 | 36 | | | | |
| | VP 16 3×(2,5 h) orally after 24 h | 6 | 36 | 1/10 | 9/10 | 107 | 16-16, 4-17 |
| | VP 16 3×(2,5 h) orally | 6 | 36 | | | | |
| 4 | VP 16 + Saran 3×(2,5 h) orally after 24 h | 4 / 35,5 | 24 / 213 | | | | |
| | VP 16 + Saran 3×(2,5 h) orally after 24 h | 4 / 35,5 | 24 / 213 | 2/10 | 8/10 | 69 | 10-11, 5-13 |
| | VP 16 + Saran 3×(2,5 h) orally | 4 / 35,5 | 24 / 213 | | | | |
| 5 | VP 16 + Saran 3×(2,5 h) orally after 24 h | 6 / 35,5 | 36 / 213 | | | | |
| | VP 16 + Saran 3×(2,5 h) orally after 24 h | 6 / 35,5 | 36 / 213 | 4/10 | 6/10 | 154 | 18-18, 2-19 |
| | VP 16 + Saran 3×(2,5 h) orally | 6 / 35,5 | 36 / 213 | | | | |
| 6 | Saran orally after 2,5 h | 35,5 | 71 | | | | |
| | Saran orally after 2,5 h | 35,5 | 71 | — | 10/10 | −2 | 8-8, 8-9 |
| | Saran orally | 35,5 | 71 | | | | |
| 7 | Saran orally after 2,5 h | 71 | 142 | | | | |
| | Saran orally after 2,5 h | 71 | 142 | — | 10/10 | 1 | 9-9, 1-10 |
| | Saran orally | 71 | 142 | | | | |

Strain: D₂B₆F₁
Tumor: L 1210
Mode of transplantation: i.p.
Body weight at start of transplantation: 25 g (average)
Date of transplantation: June 19, 1981
Start of therapy: June 22, 1981
Days of treatment: 1 + 3 times a week
Duration of therapy: 2 weeks
End of test: July 20, 1981
Number of animals/series: 10 mice

TABLE 19

| Series No. | Preparation | Single Dosage mg/kg | Total Dosage mg/kg | Cured | Died | ILS % | MST days |
|---|---|---|---|---|---|---|---|
| 1 | Control | — | — | — | 10/10 | — | 9-10-11 |
| 2 | Adriamycin iv. | 3,16 | 3,16 | — | 10/10 | 1 | 9-10,1-11 |
| 3 | Adriamycin iv. | 4,64 | 4,64 | — | 10/10 | 25 | 10-12,5-17 |
| 4 | Adriamycin iv. | 6,81 | 6,81 | — | 10/10 | 47 | 11-14,7-19 |
| 5 | Adriamycin iv. | 10 | 10 | — | 10/10 | 52 | 12-15,2-17 |
| 6 | Adriamycin + | 3,16 | 3,16 | — | 10/10 | 8 | 10-10,8-14 |

TABLE 19-continued

|   | | Single Dosage mg/kg | Total Dosage mg/kg | Cured | Died | ILS % | MST days |
|---|---|---|---|---|---|---|---|
| 7 | Adriamycin + Sarcosine iv. | 4,64 35,5 | 4,64 35,5 | 1/10 | 9/10 | 50 | 10–13,3–21 |
| 8 | Adriamycin + Sarcosine iv. | 6,81 35,5 | 6,81 35,5 | 3/10 | 7/10 | 87 | 11–13,8–16 |
| 9 | Sarcosine iv. | 35,5 | 35,5 | — | 10/10 | 8 | 9–9,2–10 |
| 10 | Sarcosine iv. | 71 | 71 | — | 10/10 | 3 | 9–9,7–14 |
| 11 | Sarcosine iv. | 142 | 142 | — | 10/10 | 5 | 9–9,5–13 |

| | |
|---|---|
| Strain: | $D_2B_6F_1$ |
| Tumor: | L 1210 |
| Mode of transplantation: | i.p. |
| Body weight at start of transplantation: | 23 g (average) |
| Date of transplantation: | July 6, 1981 |
| Start of therapy: | July 7, 1981 |
| Days of treatment: | Once a week |
| Duration of therapy: | 1 week |
| End of test: | August 6, 1981 |
| Number of animals/series: | 10 mice |

EXAMPLE 17

The test conditions used and the results obtained are given in Table 20. The series 2/3/4 show the synergistic effect of sarcosine anhydride-MTX. Folinic acid (citrovorumfactor) is always given together with MTX to reduce the toxicity of the latter.

TABLE 20

| Series No. | Preparation | Single Dosage mg/kg | Total Dosage mg/kg | Cured | Died | ILS % | MST days |
|---|---|---|---|---|---|---|---|
| 1 | Control | — | — | — | 10/10 | — | 8–8,0–8 |
| 2 | MTX iv. after 24 h Folin. sc. 3 × (2,5 h) | 40 2 | 80 12 | — | 10/10 | 80 | 13–14,4–16 |
| 3 | MTX + Sarcosine iv. after 24 h Folin. sc. 3 × (2,5 h) | 40 71 2 | 80 142 12 | 1/10 | 9/10 | 120 | 12–14,6–18 |
| 4 | MTX + Sarcosine iv. after 24 h Folin. sc. 3 × (2,5 h) | 40 142 2 | 80 284 12 | 1/10 | 9/10 | 140 | 13–16,2–22 |
| 5 | Sarcosine iv. | 71 | 142 | — | 10/10 | 3 | 8–8,2–9 |
| 6 | Sarcosine iv. | 142 | 284 | — | 10/10 | 4 | 8–8,3–9 |
| 7 | Sarcosine iv. | 284 | 568 | — | 10/10 | 3 | 8–8,2–9 |

| | |
|---|---|
| Strain: | $D_2B_6F_1$ |
| Tumor: | L 1210 |
| Mode of transplantation: | i.p. |
| Body weight at start of transplantation: | 30 g (average) |
| Date of transplantation: | March 9, 1980 |
| Start of therapy: | March 10, 1980 |
| Days of treatment: | Once a week |
| Duration of therapy: | 2 weeks |
| End of test: | April 9, 1980 |
| Number of animals/series: | 10 mice |

EXAMPLE 18

The test conditions used and the results obtained are given in Table 21. The series 4/5 show the synergistic curative effect of sarcosine-Bleomycine and the series 3 and 7 show that sarcosine when used in monotherapy is nearly as active as CPA when tested against i.m. Sarcoma 180.

TABLE 21

| Series No. | Preparation | Single Dosage mg/kg | Total Dosage mg/kg | Cured | Died | ILS % | Average difference in body weight between onset and end of experiment |
|---|---|---|---|---|---|---|---|
| 1 | Control | — | — | — | — | 10,9 ± 1,2 | −22,0% |
| 2 | Cyclophosphamide sc. | 70 | 210 | — | — | 4,7 ± 1,5 | −7,0% |
| 3 | Cyclophosphamide sc. | 140 | 420 | 5/15 | — | 1,0 ± 0,4 | −10,4% |
| 4 | Bleomycin iv. | 5 | 15 | — | — | 4,1 ± 1,2 | −5,1% |
| 5 | Bleomycin + Sarcosine iv. | 5 89 | 15 267 | 8/15 | — | 0,9 ± 0,3 | −7,3% |
| 6 | Sarcosine v. | 89 | 267 | — | — | 5,3 ± 2,0 | −3,9% |
| 7 | Sarcosine iv. | 267 | 801 | 2/15 | — | 4,4 ± 1,2 | −0,7% |

| | |
|---|---|
| Strain: | Swiss |
| Tumor: | Sarcoma 180 |
| Mode of transplantation: | i.m. |
| Body weight at start of transplantation: | 32 g (average) |
| Weight of tumor at start of treatment: | 1,2 g (average) |
| Date of transplantation: | October 26, 1979 |
| Start of therapy: | October 29, 1979 |
| Days of treatment: | 1 + 3 times a week |
| Duration of therapy: | 3 weeks |
| End of test: | November 19, 1979 |

EXAMPLE 19

The test conditions used and the results obtained are given in Table 22.

The series 2/3 ahow the synergistic curative effect of sarcosine-Spiramycine.

TABLE 22

| Series No. | Preparation | Single dosage mg/kg | Total dosage mg/kg | Cured | Died | Average weight of tumor (g) | Average difference in body weight (%) |
|---|---|---|---|---|---|---|---|
| 1 | Control | — | — | — | — | 10,9 ± 1,2 | −22,0 |
| 2 | Spiramycine iv. 2 × (4ʰ) | 40 | 240 | — | — | 6,2 ± 2,6 | −8,3 |
| 3 | Spiramycine + Sarkosine iv. 2 × (4ʰ) | 40 89 | 240 534 | 2/15 | — | 4,0 ± 2,4 | −3,2 |
| 4 | Spiramycine iv. 2 × (4ʰ) Mon. Wdn. | 40 | 480 | — | — | 6,6 ± 2,1 | −4,1 |

| | |
|---|---|
| Strain: | Swiss |
| Tumor: | Sarcoma 180 |
| Mode of transplantation: | i.m. |
| Weight of tumor at start of treatment: | 1,2 g (average) |
| Date of transplantation: | October 26, 1979 |
| Start of therapy: | October 29, 1979 |
| Days of treatment: | 1 + 3 times a week |
| Duration of therapy: | 3 weeks |
| End of test: | November 19, 1979 |
| Number of animals/series: | 15 mice |

EXAMPLE 20

The test conditions used and the results obtained are given in Table 23.

The series 4/6 show the synergistic effect of sarcosine anhydride-Vincristine and series 5 show the curative effect of sarcosine anhydride in monotherapy, all test being compared to the activity of CPA.

TABLE 23

| Series No. | Preparation | Single dosage mg/kg | Total dosage mg/kg | Cured | Died | ILS % | MST days |
|---|---|---|---|---|---|---|---|
| 1 | Control | — | — | — | 10/10 | — | 12–13, 8–17 |
| 2 | CPA sc. | 56,2 | 112,4 | 1/10 | 9/10 | 109 | 20–25, 3–31 |
| 3 | CPA sc. | 82,5 | 165 | 2/10 | 8/10 | 145 | 20–27–31 |
| 4 | Vincristine iv. | 0,216 | 0,432 | 2/10 | 8/10 | 67 | 12–12, 8–17 |
| 5 | Saran iv. | 284 | 568 | 1/10 | 9/10 | 26 | 12–13, 6–18 |
| 6 | Vincristine iv. + Saran | 0,216 284 | 0,432 568 | 4/10 | 6/10 | 127 | 12–13, 9–26 |

| | |
|---|---|
| Strain: | AKR |
| Tumor: | AKR-Leukemia (lymphocytic) |
| Mode of transplantation: | i.p. |
| Date of transplantation: | December 5, 1980 |
| Start of therapy: | December 8, 1980 |
| Days of treatment: | Once a week |
| Duration of therapy: | 2 weeks |
| End of test: | February 5, 1981 |
| Number of animals/series: | 10 |

EXAMPLE 21

The test conditions used and the results obtained are given in Table 24. The series 6/7 show the synergistic effect of sarcosine anhydride-Thymidine, compared to the activity of CPA.

TABLE 24

| Series No. | Preparation | Single dosage mg/kg | Total dosage mg/kg | Cured | Died | ILS % | MST days |
|---|---|---|---|---|---|---|---|
| 1 | control | — | — | — | 10/10 | — | 12–13,8–17 |
| 2 | CPA sc. | 56,2 | 112,4 | 1/10 | 9/10 | 109 | 20–25,3–31 |
| 3 | CPA sc. | 82,5 | 165 | 2/10 | 8/10 | 145 | 20–27–31 |
| 4 | Saran sc. | 142 | 284 | — | 10/10 | 3 | 11–14,2–27 |
| 5 | Saran sc. | 284 | 568 | — | 10/10 | 11 | 11–14,4–29 |
| 6 | Thymidine sc. | 242 | 484 | 1/10 | 9/10 | 27 | 11–15,2–30 |
| 7 | Thymidine + Saran sc. | 242 142 | 484 284 | 2/10 | 8/10 | 63 | 12–17,1–30 |

TABLE 24-continued

| | |
|---|---|
| Strain: | AKR |
| Tumor: | AKR-Leukemia (lymphocytic) |
| Mode of transplantation: | i.p. |
| Date of transplantation: | December 5, 1980 |
| Start of therapy: | December 8, 1980 |
| Days of treatment: | Once a week |
| Duration of therapy: | 2 weeks |
| End of test: | February 5, 1981 |
| Number of animals/series: | 10 |

EXAMPLE 22

The test conditions used and the results obtained are given in Table 25. The series 6/7 show the synergistic curative effect of sarcosine anhydride-Cytidine in comparision to the activity of CPA.

TABLE 25

| Series No. | Preparation | Single dosage mg/kg | Total dosage mg/kg | Cured | Died | ILS % | MST days |
|---|---|---|---|---|---|---|---|
| 1 | Control | — | — | — | 10/10 | — | 12–13,8–17 |
| 2 | CPA sc. | 56,2 | 112,4 | 1/10 | 9/10 | 109 | 20–25,3–31 |
| 3 | CPA sc. | 82,5 | 165 | 2/10 | 8/10 | 145 | 20–27–31 |
| 4 | Saran sc. | 142 | 284 | — | 10/10 | 3 | 11–14,2–27 |
| 5 | Saran sc. | 284 | 568 | — | 10/10 | 11 | 11–14,4–29 |
| 6 | Cytidine sc. | 243 | 486 | — | 10/10 | 10 | 12–14,2–27 |
| 7 | Cytidine sc. + Saran sc. | 243 142 | 486 284 | 3/10 | 7/10 | 102 | 12–14,8–33 |

| | |
|---|---|
| Strain: | AKR |
| Tumor: | AKR-Leukemia (lymphocytic) |
| Mode of transplantation: | i.p. |
| Date of transplantation: | December 5, 1980 |
| Start of therapy: | December 8, 1980 |
| Days of treatment: | Once a week |
| Duration of therapy: | 2 weeks |
| End of test: | February 5, 1981 |
| Number of animals/series: | 10 |

EXAMPLE 23

The test conditions used and the results obtained are given in Table 26. The series 2/5, 3/6 and 4/7 show the synergistic curative effect of sarcosine anhydride-Thioph. when tested against i.m. implanted Yoshida Sarcoma.

TABLE 26

| Series No. | Preparation | Single dosage mg/kg | Total dosage mg/kg | Cured | Died | Average weight of tumor (g) |
|---|---|---|---|---|---|---|
| 1 | Control | — | — | — | — | 28,7 ± 5,6 |
| 2 | Thioph. iv. after $24^h$ | 1,47 | 4,41 | 1/8 | — | 14,0 ± 2,9 |
| | Thioph. iv. | 1,47 | 4,41 | | | |
| 3 | Thioph. iv. after $24^h$ | 2,15 | 6,45 | 3/8 | — | 12,7 ± 2,2 |
| | Thioph. iv. | 2,15 | 6,45 | | | |
| 4 | Thioph. iv. after $24^h$ | 3,16 | 9,48 | 4/8 | — | 11,2 ± 1,3 |
| | Thioph. iv. | 3,16 | 9,48 | | | |
| 5 | Thioph. + Saran iv. after $24^h$ | 1,47 71 | 4,41 213 | 4/8 | — | 10,6 ± 2,1 |
| | Saran + iv. | 71 | 213 | | | |
| 6 | Thioph. + Saran iv. after $24^h$ | 2,15 71 | 6,45 213 | 6/8 | — | 12,5 ± 2,1 |
| | Thioph. + Saran iv. | 2,15 71 | 6,45 213 | | | |
| 7 | Thioph. + Saran iv. after $24^h$ | 3,16 71 | 9,48 | 8/8 | — | — |
| | Thioph. + Saran iv. | 3,16 71 | 9,48 | | | |
| 8 | Saran iv. after $24^h$ | 71 | 213 | — | — | 28,2 ± 4,4 |
| | Saran iv. | 71 | 213 | | | |
| 9 | Saran iv. after $24^h$ | 142 | 426 | — | — | 26,3 ± 4,6 |
| | Saran iv. | 142 | 426 | | | |

| | | | |
|---|---|---|---|
| Strain: | SD-rats | Days of treatment: | Twice a week |
| Tumor: | Yoshida Sarcoma | Duration of therapy: | 3 weeks |
| Mode of transplantation: | i.m. | End of test: | November 10, 1980 |

TABLE 26-continued

Date of transplantation: October 14, 1980  Number of animals/series: 8
Start of therapy: October 21, 1980

EXAMPLE 24

The test conditions used and the results obtained are given in Table 27. The series 4/5/6 show the improved effect of sarcosine and sarcosine anhydride in the form of a mixture (comparable results with lower concentrations) and the series 7/10 and 8/9 show the synergistic curative effect of mixtures of sarcosine anhydride and N-methylglycinamide and sarcosine anhydride and N-propylglycinamide, respectively.

TABLE 27

| Series No. | Preparation | Single dosage mg/kg | Total dosage mg/kg | Cured | Died | ILS % | MST days |
|---|---|---|---|---|---|---|---|
| 1 | Control | — | — | — | 15/15 | — | 7–9,4–12 |
| 2 | VM 26 iv | 6 | 12 | 0/15 | 14/15 | 58 | 8–14,8–19 |
| 3 | VM 26 iv | 12 | 24 | 6/15 | 9/15 | 183 | 9–19,2–22 |
| 4 | Sarcosine iv 5 × weekly | 356 | 3560 | 1/15 | 14/15 | 121 | 10–18,8–22 |
| 5 | Saran iv 5 × weekly | 284 | 2840 | 2/15 | 13/15 | 192 | 12–22,1–26 |
| 6 | Saran + Sarcosine 5 × weekly iv | 142 178 | 1420 1780 | 2/15 | 13/15 | 158 | 9–19,3–24 |
| 7 | N—Methyl- glycine amide iv 5 × weekly | 380 | 3800 | 0/15 | 15/15 | 114 | 9–18,1–21 |
| 8 | N—Propyl- glycine amide iv + 5 × weekly | 513 | 5130 | 0/15 | 15/15 | 107 | 9–17,3–20 |
| 9 | N—Propyl- glycine amide iv + Sarcan lv 5 × weekly | 256,5 142 | 2565 1420 | 2/15 | 13/15 | 173 | 11–20,6–22 |
| 10 | N—Methyl- glycine amide iv + Saran iv 5 × weekly | 190 142 | 1900 1420 | 1/15 | 14/15 | 169 | 10–19,3–21 |

Strain: Swiss
Tumor: Ehrlich-Carcinoma diploid
Mode of transplantation: i.c.
Body weight at start of transplantation: 32 g (average)
Date of transplantation: July 10, 1979
Start of therapy: July 11, 1979
Days of treatment: 1 + 5 times a week
Duration of therapy: 2 weeks
End of test: August 9, 1979
Number of animals/series: 15 mice

What is claimed:

1. A method for inhibiting the growth of cancer cells selected from the group consisting of leukemias, carcinomas, sarcomas and Yoshida tumor in a lower animal host which comprises the administration to the host of a growth-inhibiting pharmaceutical composition, the pharmaceutical composition comprises a mixture of (a) a compound selected from the group consisting of sarcosine anhydride, N-$C_{1-4}$-alkyl glydine, N-$C_{1-4}$-alkyl glycinamide, a pharmaceutically acceptable salt thereof or mixtures thereof, and (b) an antineoplastic chemotherapeutic selected from the group consisting of cyclophosphamide, adriamycin, cis-platinum, bleomycin, vincristine, spiramycin, thymidine, cytidine, methotrexate, thiotepa, teniposide and etoposide in a ratio of 2:1–50:1 parts by weight of a:b and a pharmaceutically acceptable adjuvant.

2. The method of claim 1 wherein the ratio is 2:1–10:1.

3. The method of claim 2 wherein 1/10 to 1/20 of the $LD_{50}$ of (b) and 1/20 to 1/100 of the $LD_{50}$ of (a) are used in said ratio.

4. The method of claim 1 wherein 1/10 to 1/20 of the $LD_{50}$ of (b) and 1/20 to 1/100 of the $LD_{50}$ of (a) are used in said ratio.

5. The method of claim 1 wherein compound (a) is sarcosine anhydride.

6. A pharmaceutical composition for inhibiting the growth of cancer cells selected from the group consisting of leukemias, carcinomas, sarcomas and Yoshida tumor in a lower animal host which comprises a mixture of (a) a compound selected from the group consisting of sarcosine anhydride, N-$C_{1-4}$-alkyl glycine, N-$C_{1-4}$-alkyl glycinamide, a pharmaceutically acceptable salt thereof or mixtures thereof, and (b) an antineoplastic chemotherapeutic selected from the group consisting of cyclophosphamide, adriamycin, cis-platinum, bleomycin, vincristine, spiramycin, thymidine, cystidine, methotrexate, thiotepa, teniposide and etoposide in a ratio of 2:1–50:1 parts by weight of a:b and a pharmaceutically acceptable adjuvant.

7. The composition of claim 6 wherein the ratio is 2:1–10:1.

8. The composition of claim 6 wherein 1/10 to 1/20 of the $LD_{50}$ of (b) and 1/20 to 1/100 of the $LD_{50}$ of (a) are used in said ratio.

9. The composition of claim 7 wherein 1/10 to 1/20 of the $LD_{50}$ of (b) and 1/20 to 1/100 of the $LD_{50}$ of (a) are used in said ratio.

10. The composition to claim 6 wherein compound (a) is sarcosine anhydride.

* * * * *